United States Patent

(12) United States Patent
Sekido

(10) Patent No.: US 11,945,172 B2
(45) Date of Patent: Apr. 2, 2024

(54) ENDOSCOPIC BENDABLE TUBE, ENDOSCOPE, AND METHOD OF MANUFACTURING ENDOSCOPIC BENDABLE TUBE

(71) Applicant: OLYMPUS CORPORATION, Tokyo (JP)

(72) Inventor: Takanori Sekido, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/864,528

(22) Filed: Jul. 14, 2022

(65) Prior Publication Data

US 2022/0347936 A1 Nov. 3, 2022

Related U.S. Application Data

(63) Continuation of application No. PCT/JP2020/002190, filed on Jan. 22, 2020.

(51) Int. Cl.
| | |
|---|---|
| *A61B 1/00* | (2006.01) |
| *A61B 1/005* | (2006.01) |
| *B29C 65/00* | (2006.01) |
| *B29C 65/16* | (2006.01) |

(52) U.S. Cl.
CPC .......... *B29C 65/16* (2013.01); *A61B 1/00073* (2013.01); *A61B 1/005* (2013.01); *A61B 1/0057* (2013.01); *B29C 66/7332* (2013.01); *B29K 2995/0026* (2013.01)

(58) Field of Classification Search
CPC . B29C 65/16; B29C 66/7332; A61B 1/00073; A61B 1/005; A61B 1/0057; A61B 1/0052; B29K 2995/0026; B23K 2101/06; B23K 2103/42; B23K 26/364; B23K 26/402; A61M 25/0105; A61M 25/0133; A61M 25/0138; A61M 25/0147
See application file for complete search history.

(56) References Cited

U.S. PATENT DOCUMENTS

| | | | |
|---|---|---|---|
| 2011/0054465 A1* | 3/2011 | Werneth | A61N 1/056 606/41 |
| 2016/0096004 A1* | 4/2016 | Gerrans | A61B 1/00096 604/95.04 |
| 2017/0079505 A1 | 3/2017 | Nakade | |

FOREIGN PATENT DOCUMENTS

| | | |
|---|---|---|
| JP | S63-315026 A | 12/1988 |
| JP | 2001-083284 A | 3/2001 |
| JP | 2007-021543 A | 2/2007 |

(Continued)

OTHER PUBLICATIONS

International Search Report dated Apr. 7, 2020 received in PCT/JP2020/002190.

*Primary Examiner* — Lauren P Farrar
*Assistant Examiner* — Hamza A Darb
(74) *Attorney, Agent, or Firm* — Scully, Scott, Murphy & Presser, P.C.

(57) ABSTRACT

An endoscopic bendable tube includes: an integrally formed resin tube; at least two wires embedded in a tube wall of the resin tube from a proximal end side to a distal end side of the resin tube, the at least two wires being parallel to a tube axis direction of the resin tube and being at positions facing each other; and a plurality of pairs of through slits formed in the tube wall of the resin tube in the tube axis direction, each pair of through slits being formed facing each other in the tube wall of the resin tube.

20 Claims, 7 Drawing Sheets

(56) References Cited

FOREIGN PATENT DOCUMENTS

| | | |
|---|---|---|
| JP | 2013-192562 A | 9/2013 |
| WO | 2016/125336 A1 | 8/2016 |
| WO | 2019/069747 A1 | 4/2019 |

\* cited by examiner

ENDOSCOPIC BENDABLE TUBE, ENDOSCOPE, AND METHOD OF MANUFACTURING ENDOSCOPIC BENDABLE TUBE

CROSS-REFERENCE TO RELATED APPLICATION

This application is a continuation of International Application No. PCT/JP2020/002190, filed on Jan. 22, 2020, the entire contents of which are incorporated herein by reference.

BACKGROUND

1. Technical Field

The present disclosure relates to an endoscopic bendable tube, an endoscope, and a method of manufacturing the endoscopic bendable tube.

2. Related Art

In the related art, an endoscope acquires image data inside a subject with an imaging device and provides treatment with a treatment tool and the like, by inserting an insertion unit into the subject such as a patient. A bendable portion of the insertion unit of the endoscope is provided with a bendable tube that is configured by coupling a plurality of pieces or the like and can be curved by operating a wire disposed in an inner surface of the pieces, making it possible to change the field of view by curving the bendable tube.

Such a bendable tube has problems such as a long time necessary for assembling the pieces, a large number of parts, and a high cost. In contrast, a bendable tube including synthetic resin (see, for example, Japanese Patent Application Laid-open No. 63-315026) and a bendable portion in which a spiral gap having a continuously changing width is formed by applying laser machining in a plate thickness direction to the outer circumference of a high-strength alloy pipe material (see, for example, Japanese Patent Application Laid-open No. 2001-83284) have been proposed.

SUMMARY

In some embodiments, an endoscopic bendable tube includes: an integrally formed resin tube; at least two wires embedded in a tube wall of the resin tube from a proximal end side to a distal end side of the resin tube, the at least two wires being parallel to a tube axis direction of the resin tube and being at positions facing each other; and a plurality of pairs of through slits formed in the tube wall of the resin tube in the tube axis direction, each pair of through slits being formed facing each other in the tube wall of the resin tube.

In some embodiments, provided is an endoscope including an endoscopic bendable tube. The endoscopic bendable tube includes: an integrally formed resin tube; at least two wires embedded in a tube wall of the resin tube from a proximal end side to a distal end side of the resin tube, the at least two wires being parallel to a tube axis direction of the resin tube and being at positions facing each other; and a plurality of pairs of through slits formed in the tube wall of the resin tube in the tube axis direction, each pair of through slits being formed facing each other in the tube wall of the resin tube.

In some embodiments, provided is a method of manufacturing an endoscopic bendable tube. The method includes: embedding at least two wires in a tube wall of a resin tube from a proximal end side to a distal end side of the resin tube such that the at least two wires is parallel to a tube axis direction of the resin tube and is at positions facing each other; fixing the resin tube to a laser device; and emitting a laser beam from the laser device on the tube wall of the fixed resin tube to form a plurality of pairs of through slits such that each pair of through slits are orthogonal to a tube axis direction and face each other, without cutting the at least two wires.

The above and other features, advantages and technical and industrial significance of this disclosure will be better understood by reading the following detailed description of presently preferred embodiments of the disclosure, when considered in connection with the accompanying drawings.

DETAILED DESCRIPTION

An endoscopic system including a bendable tube will be described below as a form for implementing the disclosure (hereinafter referred to as "embodiments"). The embodiments do not limit the disclosure. Furthermore, each figure referred to in the following description only outlines the shape, size, and positional relationship to the extent that details of the disclosure can be understood. That is, the disclosure is not limited to the shape, size, and positional relationship exemplified in each figure. Furthermore, even between the figures, parts having dimensions and ratios different from each other are included.

First Embodiment

Figure 1:
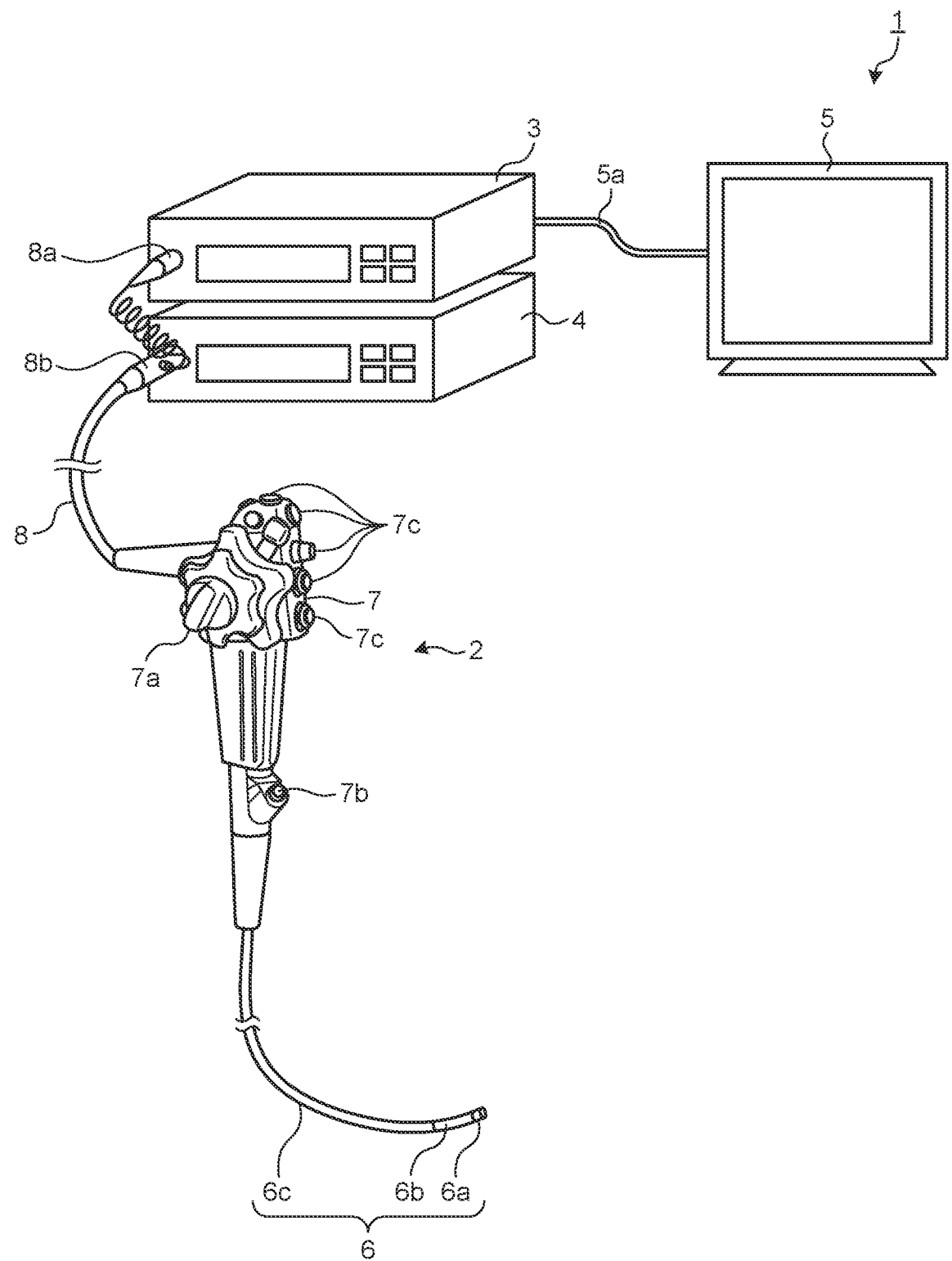
FIG. 1 is a diagram schematically illustrating an overall configuration of an endoscopic system according to a first embodiment of the disclosure.

FIG. 1 is a diagram schematically illustrating an overall configuration of an endoscopic system 1 according to a first embodiment of the disclosure. As illustrated in FIG. 1, the endoscopic system 1 according to the present embodiment includes an endoscope 2 introduced into a subject to capture an image of the inside of the subject to generate an image signal inside the subject, an information processing device 3 that performs predetermined image processing on the image signal captured by the endoscope 2 and controls each unit of the endoscopic system 1, a light source device 4 that generates illumination light for the endoscope 2, and a display device 5 that displays the image of the image signal after the image processing performed by the information processing device 3.

The endoscope 2 includes an insertion unit 6 to be inserted into the subject, an operating unit 7 on the proximal end side of the insertion unit 6 to be held by an operator, and a flexible universal cord 8 extending from the operating unit 7.

The insertion unit 6 is implemented by using a light guide including an illumination fiber, an electric cable, an optical fiber, or the like. The insertion unit 6 includes a distal end 6a with a built-in imaging device, a bendable portion 6b that can be curved and includes a bendable tube described later, and a flexible tube portion 6c having flexibility and provided on a proximal end side of the bendable portion 6b. The distal end 6a is provided with an illumination unit that illuminates the inside of the subject via an illumination lens, an observation unit that captures an image inside the subject, an aperture that allows communication of a treatment tool channel, and an air supply/water supply nozzle (not illustrated).

The operating unit 7 includes a knob 7a that causes the bendable portion 6b to be curved in an up-and-down direction and right-and-left direction, a treatment tool insertion unit 7b through which a treatment tool such as a biological forceps and laser scalpel is inserted into the body cavity of the subject, and a plurality of switch units 7c that operates peripheral devices such as the information processing device 3, the light source device 4, an air supply device, a water supply device, a gas supply device, the bendable tube, and the like. The treatment tool inserted from the treatment tool insertion unit 7b is exposed from the aperture at the distal end of the insertion unit 6 via the treatment tool channel provided inside.

The universal cord 8 is configured by using a light guide including an illumination fiber, a cable, or the like. The universal cord 8 is branched at the proximal end, one of the branched ends is a connector 8a, and the other proximal end is a connector 8b. The connector 8a is attachable and detachable to and from a connector of the information processing device 3. The connector 8b is attachable and detachable to and from the light source device 4. The universal cord 8 propagates the illumination light emitted from the light source device 4 to the distal end 6a via the connector 8b and the light guide including an illumination fiber. In addition, the universal cord 8 transmits the image signal captured by the imaging device described later to the information processing device 3 via the cable and the connector 8a.

The information processing device 3 performs predetermined image processing on the image signal output from the connector 8a, and controls the entire endoscopic system 1.

The light source device 4 is configured by using a light source that emits light, a condenser lens, and the like. Under the control of the information processing device 3, the light source device 4 emits light from the light source to supply the light to the endoscope 2 connected via the connector 8b and the light guide including an illumination fiber of the universal cord 8 as illumination light for the inside of the subject, which is an object.

The display device 5 is configured by using a display using a liquid crystal display, organic electro luminescence (EL), or the like. The display device 5 displays various information items including an image that has undergone predetermined image processing by the information processing device 3 via a video cable 5a. This allows the operator to observe a desired location inside the subject and determine symptoms by operating the endoscope 2 while looking at the image (in-vivo image) displayed by the display device 5.

Figure 2:
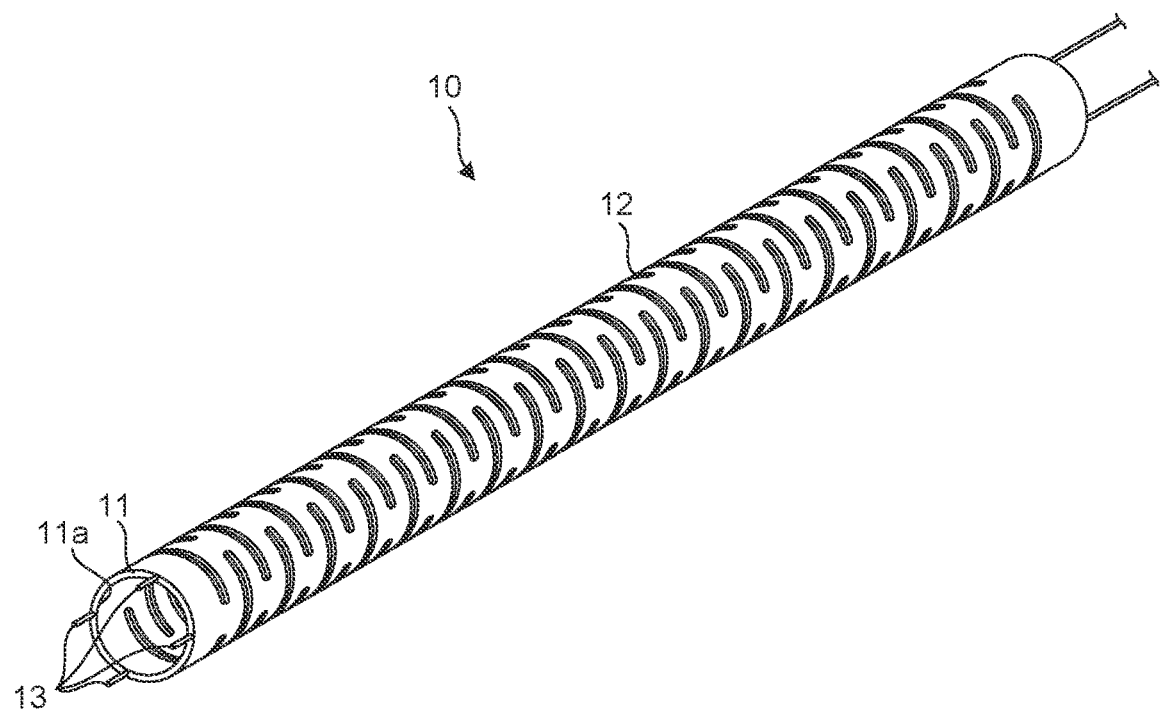
FIG. 2 is a perspective view of a bendable tube to be used in an endoscope according to the first embodiment of the disclosure.
Figure 3:
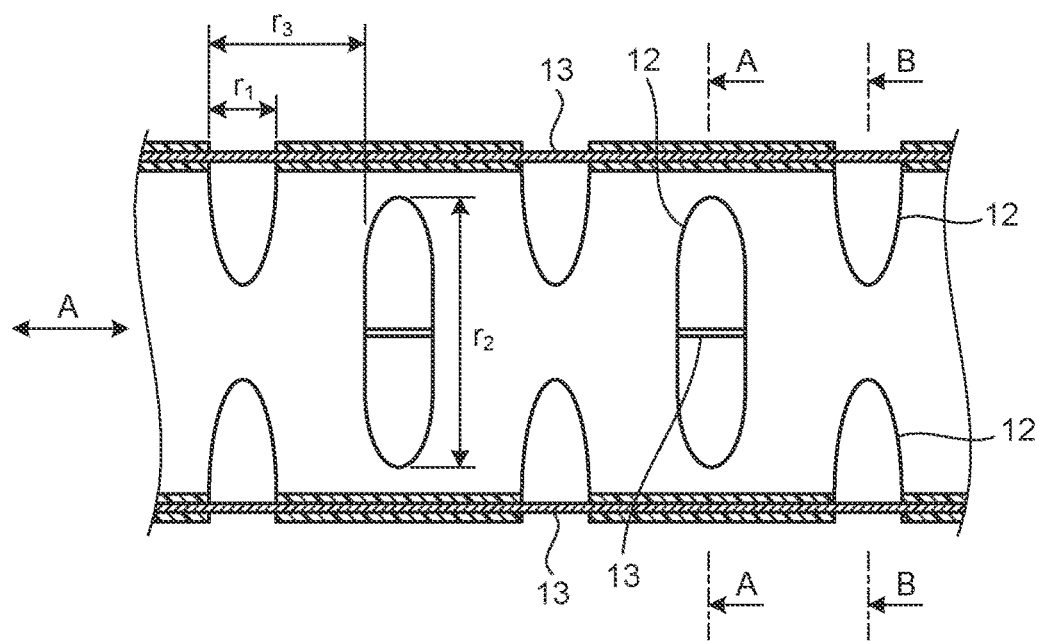
FIG. 3 is a cross-sectional view of the bendable tube of FIG. 2.

Next, the bendable tube used in the endoscopic system 1 will be described in detail. FIG. 2 is a perspective view of a bendable tube 10 used in the endoscope 2 according to the first embodiment of the disclosure. FIG. 3 is an enlarged cross-sectional view in a plane including a tube axis of the bendable tube 10 of FIG. 2.

The bendable tube 10 includes a resin tube 11, four wires 13 embedded in a tube wall of the resin tube 11 from a proximal end side to a distal end side of the resin tube 11 at positions parallel to a tube axis direction of the resin tube 11 and facing each other, and a plurality of pairs of through slits 12 formed in the tube wall of the resin tube 11 in the tube axis direction, each pair of through slits 12 being formed facing each other in the tube wall of the resin tube 11. The bendable portion 6b is formed by covering the outer circumference of the bendable tube 10 with a blade, and further covering the blade with an outer covering.

The resin tube 11 is configured by using synthetic resin and includes a through hole 11a into which the treatment tool channel, the light guide, the cable, and the like are inserted. When used for the bendable tube 10 of the bendable portion 6b of the endoscope 2, the resin tube 11 has a size, for example, with the outer diameter of 0.5 mm to 20.0 mm, the inner diameter of 0.3 mm to 19.8 mm, the length of 1.0 cm to 10.0 cm, and the thickness of the tube wall of about 0.1 mm.

The distal end side of the wires 13 is fixed to the distal end 6a of the endoscope 2, and the proximal end side is connected to the knob 7a. The bendable tube 10 is curved by pulling or relaxing the wires 13 by operating the knob 7a. The four wires are embedded inside the resin tube 11 approximately every 90° in the circumferential direction.

Figure 4:
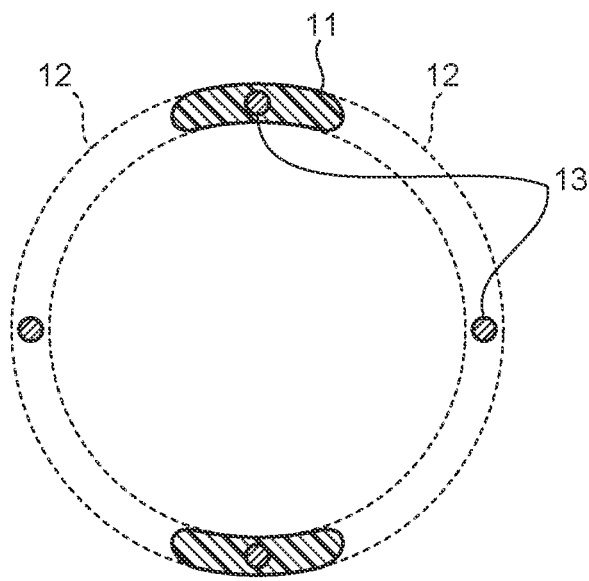
FIG. 4 is a cross-sectional view taken along the line A-A of FIG. 3.
Figure 5:
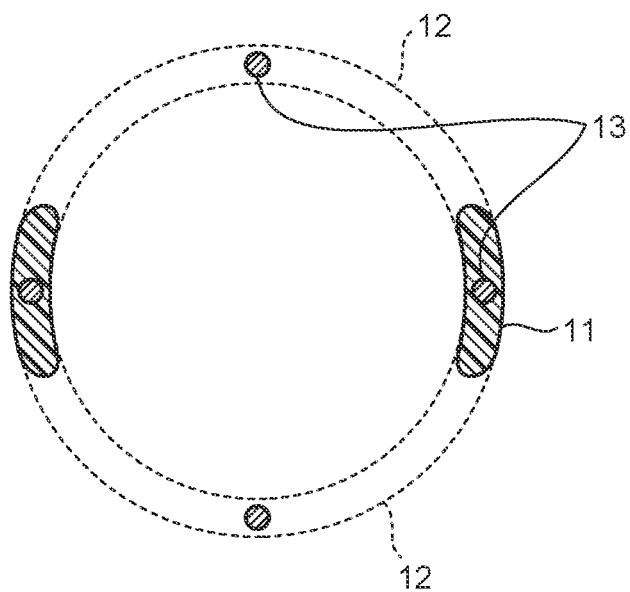
FIG. 5 is a cross-sectional view taken along the line B-B of FIG. 3.

The through slit 12 is a slit penetrating the tube wall of the resin tube 11, and the length direction r2 is orthogonal to the tube axis direction A and is formed along the circumference of the resin tube 11. At the same position in the tube axis direction A of the resin tube 11, two through slits 12 are formed facing each other, and the plurality of through slits 12 is formed at equal intervals along the tube axis direction A of the resin tube 11. Furthermore, the through slits 12 adjacent in the tube axis direction A are formed at positions rotated by 90° in the circumferential direction as illustrated in FIGS. 4 and 5. FIG. 4 is a cross-sectional view taken along the line A-A of FIG. 3, and FIG. 5 is a cross-sectional view taken along the line B-B of FIG. 3. At the position of the A-A line illustrated in FIG. 4, the through slits 12 are provided facing each other in the right-and-left direction of the paper surface, and the through slits 12 at the position of the B-B line adjacent to the position of the A-A line illustrated in FIG. 5 are formed facing each other in the up-and-down direction of the paper surface rotated by 90° from the through slits 12 at the position of the A-A line.

The through slit 12 is preferably configured such that: the width r1 is equal to or greater than the thickness of the tube wall of the resin tube 11 and less than the outer diameter of the resin tube 11; the length r2 is equal to or greater than ½ of the outer circumference of the resin tube 11−width r1×3 and less than ½ of the outer circumference of the resin tube 11−width r1; and the pitch r3 is equal to or greater than the thickness of the tube wall of the resin tube 11. By setting the width r1, the length r2, and the pitch r3 of the through slit 12 in the above range, the curving operation of the bendable tube 10 is easy.

Figure 6:
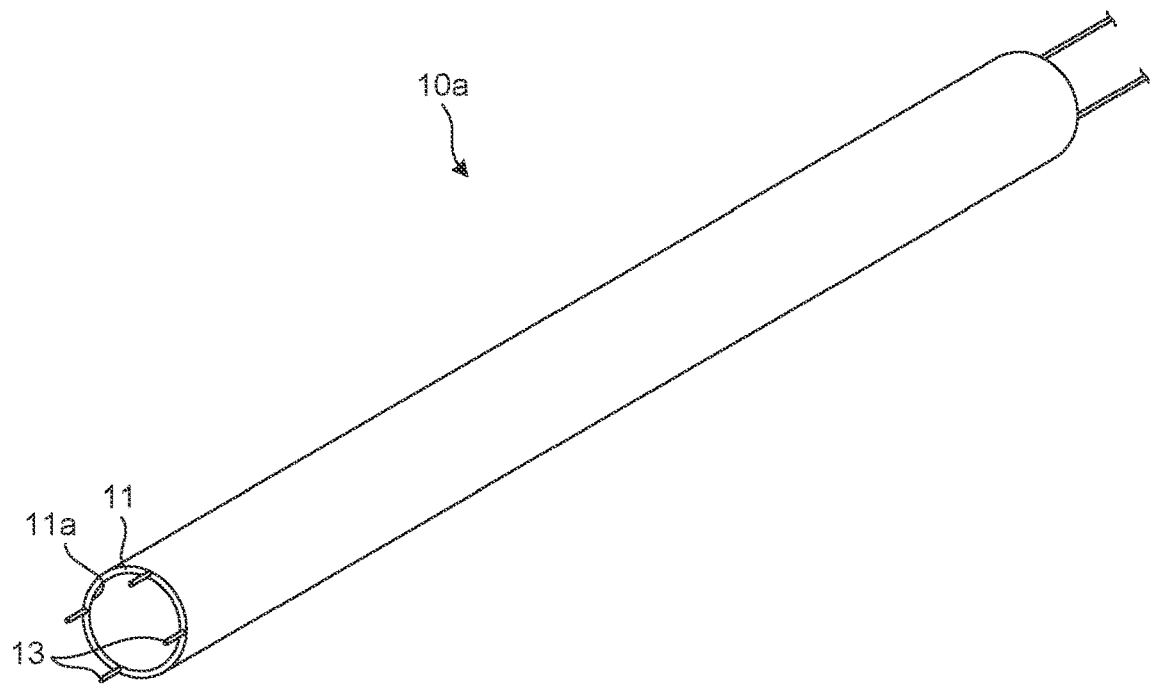
FIG. 6 is a perspective view of the bendable tube before forming through slits.

FIG. 6 is a perspective view of a bendable tube 10a before forming the through slits 12. The bendable tube 10a has four wires 13 embedded at positions parallel to the axis direction of the resin tube 11 and facing each other from the proximal end side to the distal end side of the resin tube 11 in the tube wall of the resin tube 11.

The bendable tube 10 can be manufactured by fixing the bendable tube 10a to a laser device, using a laser beam emitted from the laser device on the tube wall of the resin tube 11 of the bendable tube 10a, and forming the plurality of through slits 12 orthogonal to the tube axis direction A and facing each other without cutting the wires 13. Note that the through slit 12 may have a form in which the resin tube 11 around the wire 13 on the tube axis center side of the wire 13 remains, but from the viewpoint of the ease of curving the bendable tube 10, the through slit 12 preferably has a form in which the resin tube 11 around the wire 13 is completely removed.

The laser device to use is preferably emits a carbon dioxide laser beam. By using the carbon dioxide laser beam, even if the metal wire 13 is irradiated with the laser beam, the bendable tube 10 having excellent quality can be manufactured without cutting the wire 13. Furthermore, from the viewpoint of accuracy of the shape and the like and costs of the through slit 12, it is preferable to form the through slit 12 with a laser beam, but the disclosure is not limited to this example, and the through slit 12 can also be formed by plasma ashing or the like.

The cost of the bendable tube 10 according to the first embodiment can be reduced by using the resin tube 11. In addition, since the wires 13 are embedded in the resin tube 11, it is not necessary to separately provide a wire guide in the resin tube 11. Therefore, the wall thickness of the resin tube 11 can be reduced by the wire guide, and the diameter of the bendable tube can be reduced. In addition, the process of inserting wires into the wire guide can also be reduced.

Note that in the first embodiment, only the wires 13 are embedded in the resin tube 11, but the light guide and the cable may also be embedded in the resin tube 11.

Second Embodiment

Figure 7:
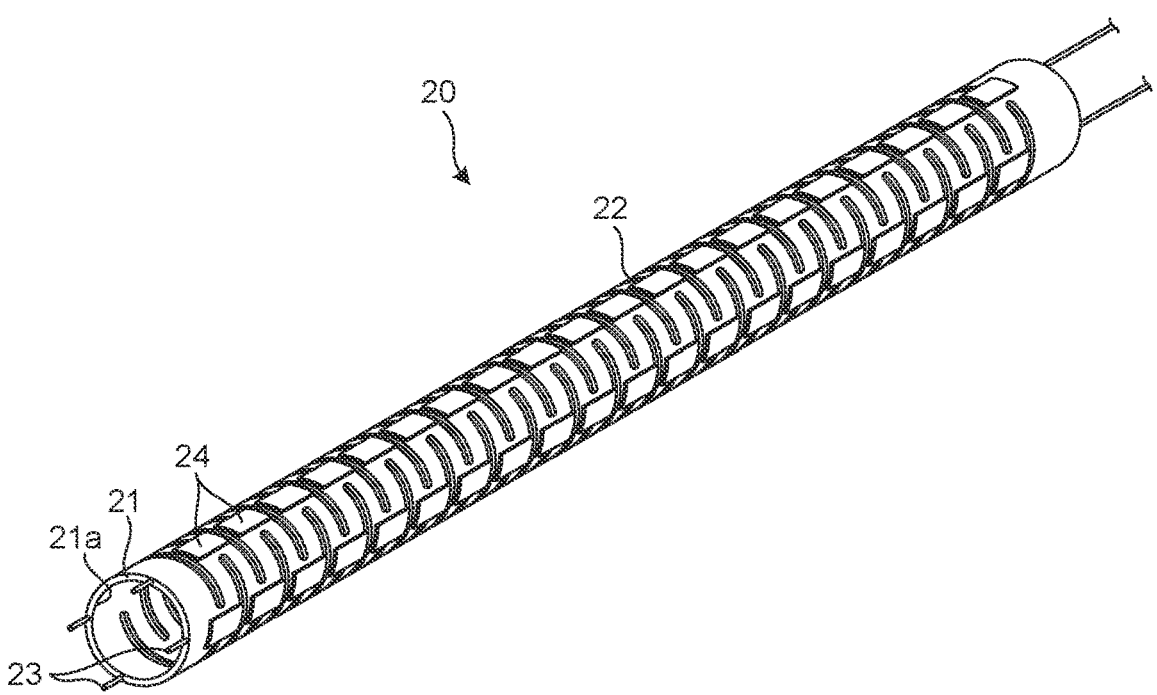
FIG. 7 is a perspective view of a bendable tube according to a second embodiment of the disclosure.

FIG. 7 is a perspective view of a bendable tube 20 according to a second embodiment of the disclosure. The bendable tube 20 includes a resin tube 21, through slits 22, wires 23, and a metal pattern 24.

The metal pattern 24 may be formed by forming a metal film on an outer wall surface of the resin tube 21 by sputtering or the like, and then removing the metal film of an area other than a desired area of the outer wall surface of the resin tube 11 by photolithography or laser machining. The metal pattern 24 may be formed by forming a covering member that covers an area other than the desired area on the entire surface of the resin tube 21, and then forming a metal film on the covering member and the entire exposed portion of the resin tube 21 by sputtering or the like, and further removing the covering member. The metal pattern 24 may be formed by printing a metal-containing ink on a desired area and then curing the ink.

Figure 8:
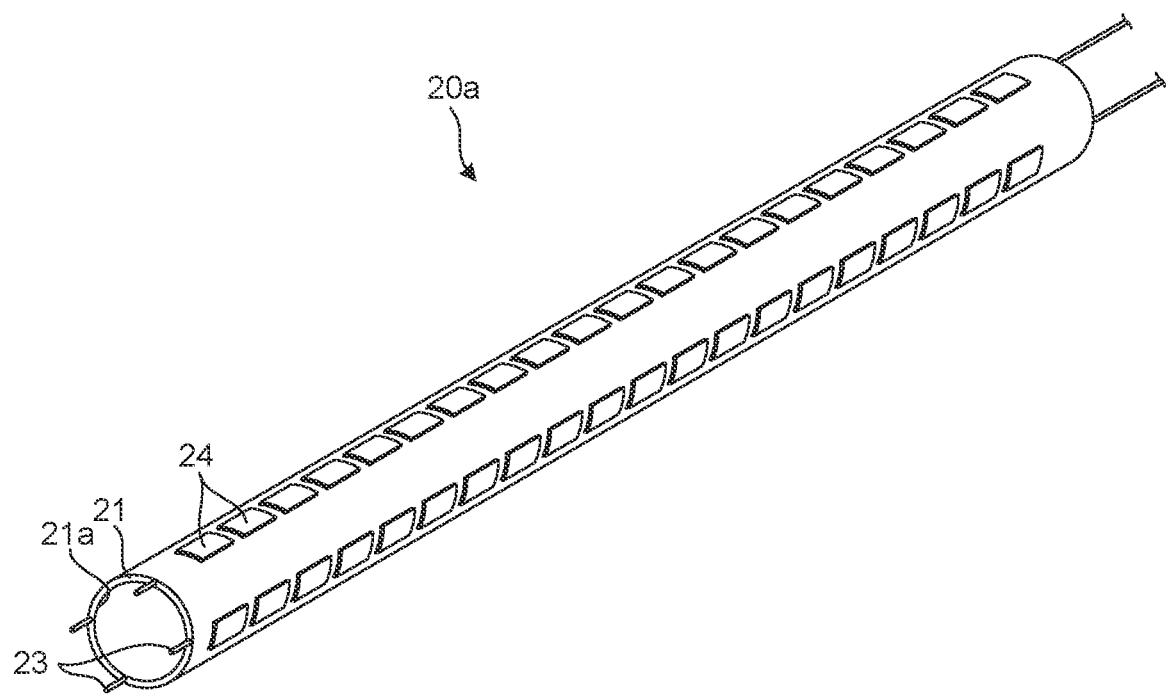
FIG. 8 is a perspective view of the bendable tube before forming through slits.

FIG. 8 is a perspective view of a bendable tube 20a before forming the through slits 22. The bendable tube 20a is obtained by forming the metal pattern 24 on the outer wall surface of the resin tube 21 after embedding the wires 23 in the resin tube 21.

The bendable tube 20 is manufactured by using a laser beam emitted from a laser device on a tube wall of the resin tube 21 of the bendable tube 20a to form the plurality of through slits 22 orthogonal to the tube axis direction and facing each other without cutting the wires 23. Laser machining may machine (remove) the periphery of a region to machine due to reflected light, scattered light, and heat generated during machining. If both ends of the through slit corresponding to a joint of bendable structure are machined (removed), the bendable structure may not be obtained. In the present embodiment, since the metal pattern 24 is not machined by a carbon dioxide laser beam, it is possible to prevent laser machining on the periphery of the region to machine by forming the metal pattern 24 in an area that does not undergo laser machining.

In addition to effects of the first embodiment, the bendable tube 20 according to the second embodiment has an effect that the through slits 22 can be formed with high accuracy.

Third Embodiment

Figure 9:
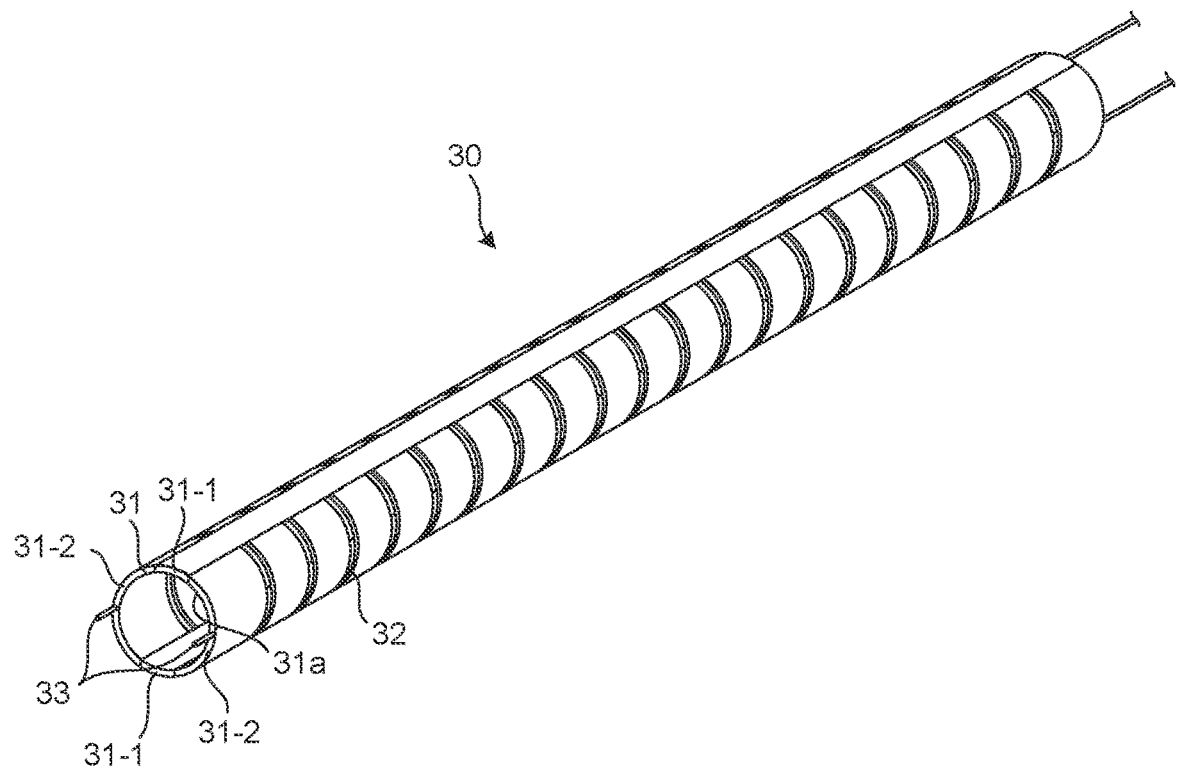
FIG. 9 is a perspective view of a bendable tube according to a third embodiment of the disclosure.
Figure 10:
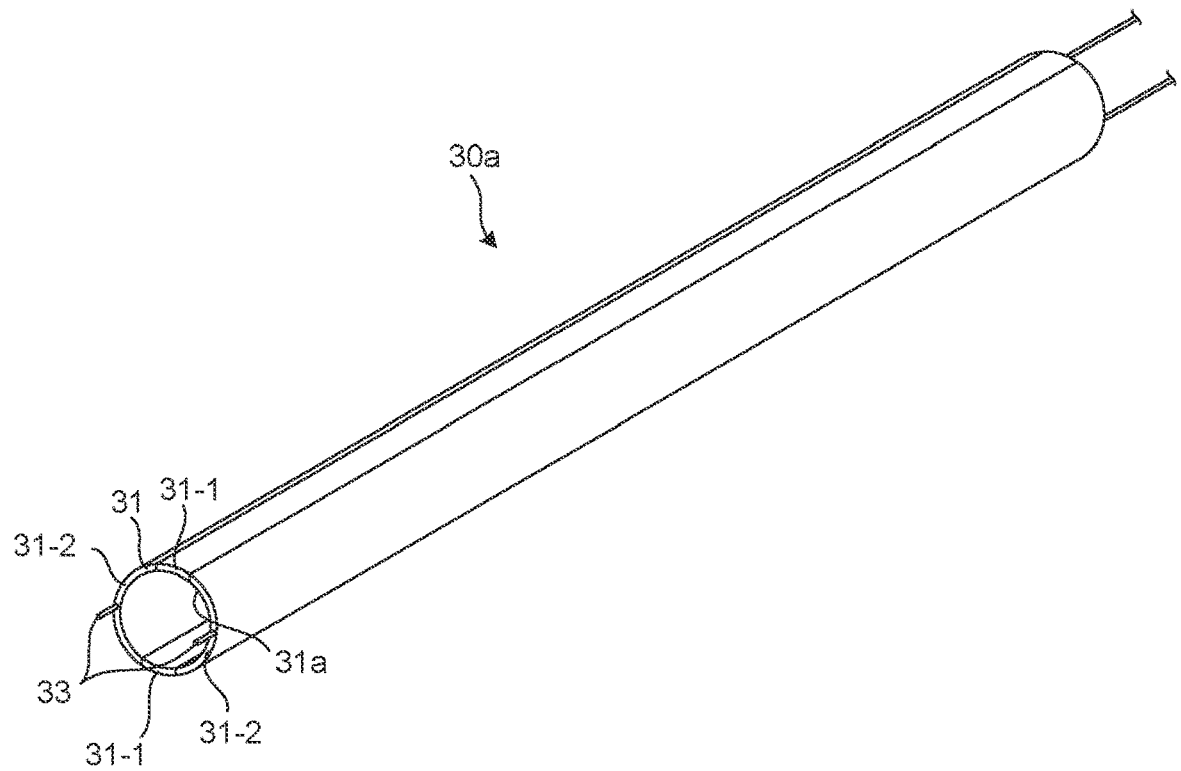
FIG. 10 is a perspective view of the bendable tube before forming through slits.

FIG. 9 is a perspective view of a bendable tube 30 according to a third embodiment of the disclosure. The bendable tube 30 includes a resin tube 31, through slits 32, and two wires 33. The bendable tube 30 is curved by the two wires 33 in one of two directions, up-and-down and right-and-left directions.

The resin tube 31 is formed using a transparent or light-colored resin area 31-1 that does not easily absorb a carbon dioxide laser beam, and a dark-colored resin area 31-2 that absorbs the carbon dioxide laser beam. Here, the light color is preferably white, but may be other than white as long as the color is a light color that does not easily absorb the carbon dioxide laser beam. Meanwhile, the dark color is preferably black, but may be other than black as long as the color is a dark color that absorbs the carbon dioxide laser beam. The transparent or light-colored resin area 31-1 is provided to extend from the proximal end side to the distal end side of the resin tube 31 and to face each other with the tube axis as the center. The dark-colored resin area 31-2 is provided to extend from the proximal end side to the distal end side of the resin tube 31 and to face each other with the tube axis as the center, and ends are continuous to be in contact with the transparent or light-colored resin area 31-1. The resin tube 31 can be formed by two-color molding using a transparent or light-colored resin and a dark-colored resin.

The two wires 33 are embedded in the tube wall of the black resin area 31-2 from the proximal end side to the distal end side of the resin tube 31 at positions parallel to the tube axis direction of the resin tube 31 and facing each other.

Through slits 32 are formed facing each other in the tube wall of the black resin area 31-2, and a plurality of the through slits is formed in the tube axis direction. Laser machining may machine (remove) the periphery of the region to machine due to reflected light, scattered light, and heat generated during machining, but the transparent or white resin area 31-1, which does not easily absorb the carbon dioxide laser beam, is unlikely to undergo laser machining. By forming the area that does not undergo laser machining using a transparent or white resin, it is possible to prevent machining by a laser beam on the periphery of the region to machine.

In addition to effects of the first embodiment, the bendable tube 30 according to the third embodiment can form the through slits 32 with high accuracy, and can mold the resin tube 31 including the transparent or white resin area 31-1 and the black resin area 31-2 by two-color molding technology, and therefore has an effect of reducing manufacturing costs.

Note that in the third embodiment described above, the resin tube 31 is formed by using the transparent or white resin area 31-1 that does not easily absorb the carbon dioxide laser beam and the black resin area 31-2 that absorbs the carbon dioxide laser beam. However, as the resin that does not easily absorb the carbon dioxide laser beam, a resin containing a metal fiber filler can also be used. The resin containing a metal fiber filler, which does not easily absorb the carbon dioxide laser beam, is unlikely to undergo laser machining. By forming the area that does not undergo laser machining using the resin containing a metal fiber filler, it is possible to prevent machining by a laser beam on the periphery of the region to machine.

Fourth Embodiment

Figure 11:
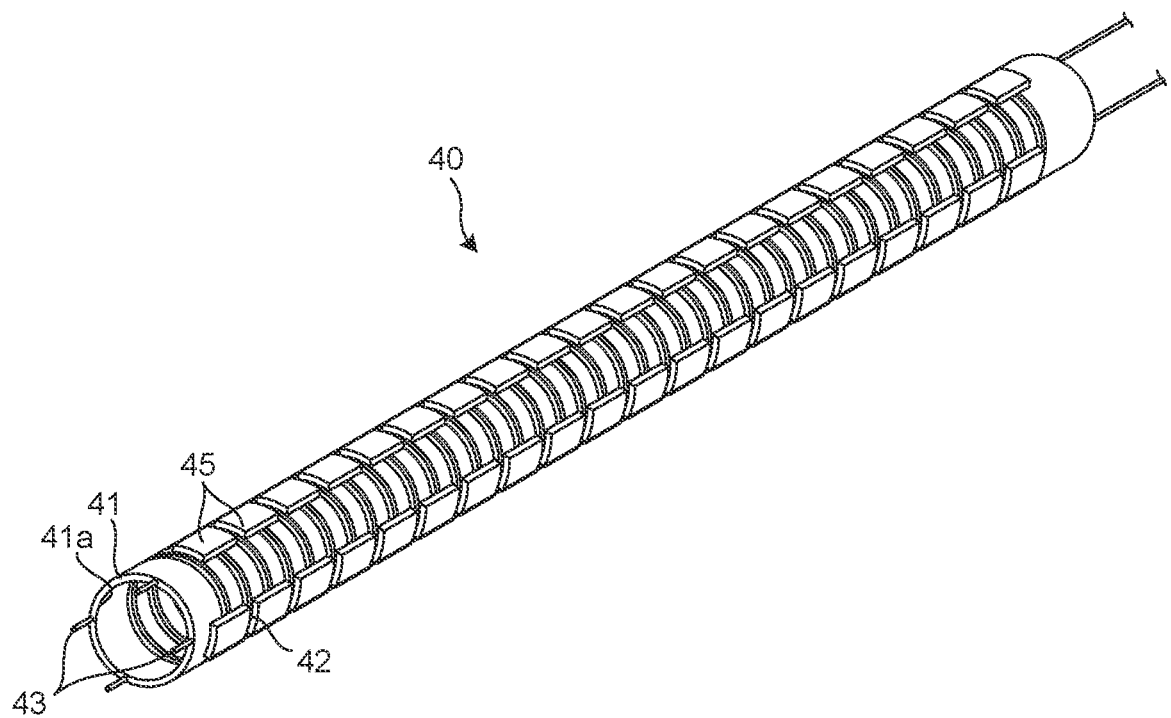
FIG. 11 is a perspective view of a bendable tube according to a fourth embodiment of the disclosure.
Figure 12:
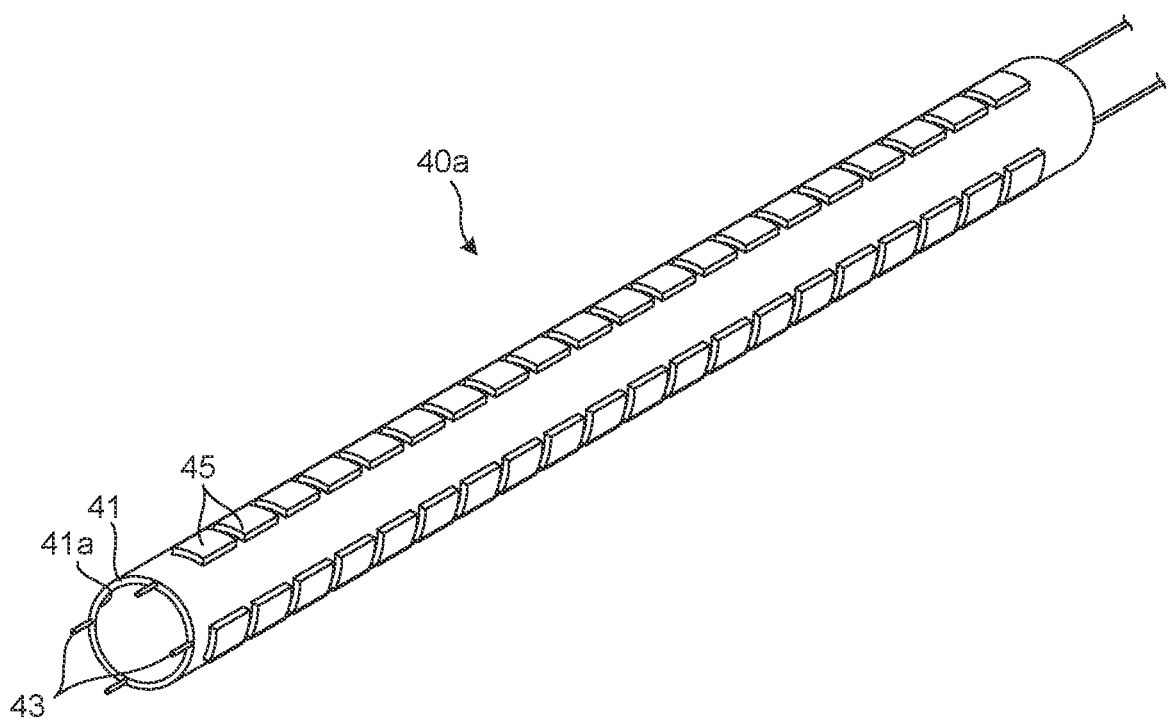
FIG. 12 is a perspective view of the bendable tube before forming through slits.

FIG. 11 is a perspective view of a bendable tube 40 according to a fourth embodiment of the disclosure. The bendable tube 40 includes a resin tube 41, through slits 42, and four wires 43.

The resin tube 41 includes an area 45 with a thick tube wall. In the resin tube 41, after obtaining a resin tube with a uniform wall thickness, the area 45 with a thick tube wall can be formed by pressing or the like. By setting an area that does not undergo laser machining as the area 45 with a thick tube wall, it is possible to prevent machining by a laser beam on the periphery of the region to machine.

In addition to effects of the first embodiment, the bendable tube 40 according to the fourth embodiment has an effect that the through slits 42 can be formed with high accuracy and manufacturing costs can be reduced.

The disclosure allows omission of the wire guide formation process and the wire insertion process, making it possible to manufacture the endoscopic bendable tube easily and at low cost, and to reduce the diameter of the endoscopic bendable tube because wires are embedded inside the tube wall.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic bendable tube comprising:
a resin tube extending in a longitudinal direction;
at least two wires disposed in the resin tube to extend in the longitudinal direction from a proximal end side to a distal end side of the resin tube; and
a plurality of slit pairs formed in a first area of a wall of the resin tube, the plurality of slit pairs arranged at intervals in the longitudinal direction of the resin tube, a first pair of slit ends oppose each other across a second area of the wall of the resin tube;
wherein a second radial thickness of the wall of the resin tube in the second area is greater than a first radial thickness of the wall of the resin tube in the first area.

2. The endoscopic bendable tube according to claim 1, wherein the second area comprises a metal formed on an outer surface of the resin tube.

3. An endoscope comprising the endoscopic bendable tube according to claim 1.

4. The endoscope according to claim 3, wherein the second area comprises a metal formed on an outer surface of the resin tube.

5. The endoscopic bendable tube according to claim 1, wherein the at least two wires comprise four wires equally spaced from each other circumferentially.

6. The endoscopic bendable tube according to claim 5, wherein
the plurality of slit pairs comprise a plurality of first slit pairs and the slit ends comprise first slit ends;
further comprising a plurality of second slit pairs, each second slit pair of the plurality of second slit pairs being formed in a third area of a wall of the resin tube and disposed between adjacent first slit pairs of the plurality of first slit pairs such that a second pair of second slit ends oppose each other across a fourth area of the wall of the resin tube, and
wherein a fourth radial thickness of the wall of the resin tube in the fourth area is greater than a third radial thickness of the wall of the resin tube in the third area.

7. The endoscopic bendable tube according to claim 6, wherein each second area is offset circumferentially from an adjacent fourth area.

8. The endoscopic bendable tube according to claim 7, wherein each second area is offset circumferentially 90 degrees from the adjacent fourth area.

9. The endoscopic bendable tube according to claim 1, wherein each slit pair of the plurality of slit pairs face each other across the longitudinal axis.

10. The endoscopic bendable tube according to claim 1, wherein the resin tube is integrally formed.

11. The endoscopic bendable tube according to claim 1, wherein the at least two wires are embedded in the wall of the resin tube.

12. An endoscopic bendable tube comprising:
a resin tube extending in a longitudinal direction;
at least two wires disposed in the resin tube to extend in the longitudinal direction from a proximal end side to a distal end side of the resin tube; and
a plurality of slit pairs formed in a first area of a wall of the resin tube, the plurality of slit pairs arranged at intervals in the longitudinal direction of the resin tube, a first pair of slit ends oppose each other across a second area of the wall of the resin tube;
wherein at least a portion of a second material of the wall of the resin tube in the second area is different than a first material of the wall of the resin tube in the first area, the first material being configured to absorb a carbon dioxide laser beam more than at least the portion of the second material.

13. The endoscopic bendable tube according to claim 12, wherein at least the portion of the second material comprises metal.

14. The endoscopic bendable tube according to claim 12 wherein at least the portion of the second material is a first resin, and the first material is a second resin.

15. The endoscopic bendable tube according to claim 14, wherein at least the portion of the first resin is a transparent or light-colored resin, and the second resin is a dark-colored resin.

16. The endoscopic bendable tube according to claim 14, wherein at least the portion of the first resin contains a metal filler, and the second resin contains no metal filler.

17. The endoscopic bendable tube according to claim 12, wherein each slit pair of the plurality of slit pairs face each other across the longitudinal axis.

18. The endoscopic bendable tube according to claim 12, wherein the resin tube is integrally formed.

19. The endoscopic bendable tube according to claim 12, wherein the at least two wires comprise four wires equally spaced from each other circumferentially.

20. The endoscopic bendable tube according to claim 12, wherein the at least two wires are embedded in the wall of the resin tube.

\* \* \* \* \*